United States Patent [19]

Wielinger et al.

[11] Patent Number: 5,783,759
[45] Date of Patent: Jul. 21, 1998

[54] ELEMENT AND SYSTEM FOR COLLECTING, TRANSPORTING AND STORING SAMPLE MATERIAL TO BE ANALYZED

[75] Inventors: Hans Wielinger, Weinheim; Rolf Lerch, Ilvesheim; Wolfgang Werner, Mannheim, all of Germany

[73] Assignee: Boehringer Mannheim GmbH, Mannheim, Germany

[21] Appl. No.: 668,916

[22] Filed: Jun. 24, 1996

[30] Foreign Application Priority Data

Jun. 24, 1995 [DE] Germany ............. 195 23 061.2

[51] Int. Cl.$^6$ .................. G01N 1/10; G01N 1/18
[52] U.S. Cl. ........................................ 73/864.72
[58] Field of Search ................. 73/864.71, 864.72, 73/84.56

[56] References Cited

U.S. PATENT DOCUMENTS

| | | | |
|---|---|---|---|
| 2,902,146 | 9/1959 | Doherty | 73/864.72 X |
| 3,282,114 | 11/1966 | Pell | 73/864.72 |
| 3,496,777 | 2/1970 | Packer et al. | 73/864.72 |
| 4,175,439 | 11/1979 | Laker | 73/864.72 |
| 4,308,028 | 12/1981 | Elkins | 73/864.72 X |
| 4,539,182 | 9/1985 | Johnson et al. | 73/864.72 X |
| 4,849,340 | 7/1989 | Oberhardt | 73/864.72 X |
| 5,213,766 | 5/1993 | Flesher et al. | 73/864.72 X |

FOREIGN PATENT DOCUMENTS

| | | | |
|---|---|---|---|
| 185982 | 7/1986 | European Pat. Off. | |
| 2424426 | 3/1975 | Germany | 73/864.72 |

*Primary Examiner*—Thomas P. Noland
*Attorney, Agent, or Firm*—Felfe & Lynch

[57] ABSTRACT

Disclosed is an element for collecting, transporting and storing sample material to be analyzed containing absorptive matrix material. The element contains a first and a second layer of absorptive matrix material which are arranged side by side, next to, and touching one another on an inert support material in a contact enabling liquid transfer in such a manner that liquid can pass from the first into the second layer when the first layer is filled with liquid. The first layer can be completely separated from the second layer after applying and drying the sample material. Also disclosed is a system containing such an element and a closable envelope in which the element can be transported. In addition, the invention concerns a method for analyzing a liquid sample material in which the liquid sample material is applied to an element according to the invention, the first layer is separated from the second layer of absorptive matrix material for analysis and is subsequently eluted.

12 Claims, 1 Drawing Sheet

ELEMENT AND SYSTEM FOR COLLECTING, TRANSPORTING AND STORING SAMPLE MATERIAL TO BE ANALYZED

BACKGROUND OF THE INVENTION

The invention concerns an element for collecting, transporting and storing sample material to be analyzed containing absorptive matrix material. The invention additionally concerns a system containing such an element and a closable envelope in which the element can be transported. In addition the invention concerns a method for analyzing liquid sample material in which it is applied to an absorptive matrix material, dried there and is transported to an analytical station, eluted from the matrix material for analysis and to form a solution and this solution is analyzed. The transport of sample material from patients into a laboratory is an important step in obtaining an analytical result. Based on the analytical result the doctor makes a diagnosis and thus for example assesses the metabolic status of patients with diabetes, disorders of fat metabolism, hormone disorders etc.. Usually body fluids are analyzed directly by the attending doctor or transported in transport vials to a laboratory. The transport of such samples is complicated and involves risks such as breakage of the transport vial. Even if only small amounts of sample are needed for an analysis, often large amounts must nevertheless be collected for such a transport. Thus a venipuncture is often necessary if it is intended to examine blood in a laboratory although a simple collection of capillary blood from for example the finger pad would suffice.

For these reasons there have been no lack of attempts in developing withdrawal and transport systems for capillary blood, especially for the quantitative determination of substances that is possible from a small amount of sample material such as for example the Unisept® system from Owen Mumford Ltd., Oxford, Great Britain. This system is described for example in Scand. J. Clin. Lab. Invest. 46, 315–317 (1986). This can be used to withdraw capillary blood as such for the subsequent determination of $HbA_{1c}$, to store it in a liquid form and transport it to the site of analysis. It can be appreciated that the transport of such liquid containers is complicated and implies a considerable risk of breakage and thus also of infection.

A method of transporting also smaller amounts of sample material to the site of analysis is described for example in Br. Med. J. 2, 468–469 (1978). For the determination of glucose capillary blood is applied to filter paper and allowed to dry onto it. This filter paper is then transported as such to the site of the examination. There a disk containing sample is cut out, eluted and the eluate is examined. In this process inaccuracies result through variations in the size of the cut out disk and by different spreading properties of the applied blood samples which are explained by the different content of blood cells in the sample. The requirement of cutting out a paper disk from the filter paper also means in this method there is a complicated handling of potentially infectious material.

The object of the present invention is therefore to provide an element for collecting, transporting and storing sample material to be analyzed containing absorptive matrix material which facilitates the handling of dried sample liquids and ensures the most homogeneous possible distribution of the sample.

SUMMARY OF THE INVENTION

The above-stated object is achieved by the invention.

The invention concerns an element for collecting, transporting and storing sample material to be analyzed containing absorptive matrix material. The element contains a first and a second layer of an absorptive matrix material arranged next to and touching one another on an inert support material in a contact enabling transfer of liquid in such a manner that liquid can pass from the first into the second layer when the first layer is filled with liquid and the first layer can be completely separated from the second layer after applying and drying the sample material.

The invention also concerns a system containing an element according to the invention and a closable envelope in which the element can be transported.

In addition the invention concerns a method for analyzing liquid sample material in which liquid sample material is applied to an absorptive matrix material, dried there and is transported to an analytical station, eluted from the matrix material with formation of a solution for analysis and this solution is analyzed which is characterized in that the liquid sample material is applied to the first layer of absorptive matrix material of an element and for analysis the first layer is separated from the second layer of absorptive matrix material and is subsequently eluted.

DESCRIPTION OF PREFERRED EMBODIMENT

Figure 1:
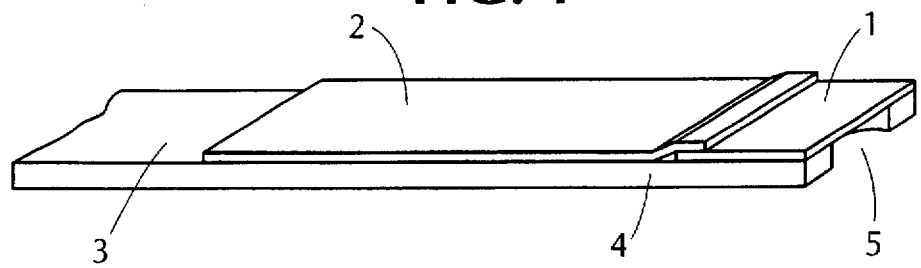
FIG. 1 is a perspective view of a preferred embodiment of an element of the invention.

The various features of novelty which characterize the invention are pointed out with particularity in the claims annexed to and forming a part of this specification. For a better understanding of the invention, its operating advantages and specific objects obtained by its use, reference should be had to the accompanying drawings and descriptive matter in which there is illustrated and described a preferred embodiment of the invention.

The element according to the invention is formed of an inert support and a first and second layer of an absorptive matrix material, the first and second layers, on at least one side, being positioned adjacent to one another in a touching or overlapping arrangement and is suitable for collecting, transporting and storing sample material to be analyzed, in particular liquid samples and such as body fluids such as blood, plasma, serum, urine, saliva etc. The element according to the invention is particularly preferably used to collect, transport and store blood samples. The two layers of absorptive matrix material are arranged on the inert support material such that liquid transfer from the first into the second layer is possible when the first layer is saturated filled with liquid.

Fibrous materials are preferably used as absorptive matrix materials although in principle non-fibrous materials such as for example membranes can also be used. Preferred fibrous absorptive matrix materials are fleeces, fabrics or woven fabrics. Fleeces are quite especially preferred. The fibrous matrix materials can contain glass, cellulose, polyester fibres and also viscose and polyvinylalcohol. Fleece materials containing meltable copolyester fibres in addition to glass fibres, polyester fibres, polyamide fibres, cellulose fibres or cellulose derivative fibres as described in the U.S. Pat. No. 5,478,751 can also be used advantageously in the element according to the invention.

Depending on the analyte to be analyzed it must be ensured that the analyte can subsequently be reproducibly eluted again after the sample material has been applied and dried onto the absorptive matrix material and in particular the matrix material of the first layer. For this purpose a person skilled in the art can carry out simple and routine elution experiments to identify the preferred matrix material.

Attention must be paid to the absorptivity as an important property of the absorptive matrix materials that can be used according to the invention. According to the invention, the absorptivity of the matrix material of the first layer should be equal to, or larger than, that of the second neighboring layer. This avoids interfering absorptive effects from occurring when the sample material is applied to the first layer.

The absorptivity can be determined according to DIN 53106 (German Industrial Standard). For this the lower end of matrix samples of 200+/−1 mm in length and 15+/−0.1 mm in width are immersed perpendicularly 25 mm into distilled water and the path which the water travels in 10 minutes is measured in mm.

It is known to a person skilled in the art how different absorptivities can be adjusted in matrix materials with the same components. For example fibres of different thickness can be used when manufacturing fleeces. The thicker the fibres used the lower is the absorptivity. A further method is to vary the density of fleeces. The absorptivity is reduced by increasing the density.

When using fabrics, fabrics with finer fibres have a larger absorptivity than fabrics with coarser fibres.

The absorptivity can also be controlled by different types of twisting the threads. In addition differences in absorptivity can be achieved by the types of weaving.

Further possibilities of varying the absorptivity are to use different fibre mixtures. Thus for example addition of hydrophobic fibres lowers the absorptivity.

Stiff materials such as for example plastic foils, cardboard, coated paper etc. come especially into consideration as the inert support material for the two matrix material layers used according to the invention.

The matrix material layers are fixed onto the inert support material in such a way that the liquid uptake by the matrix materials is not impaired. This can be achieved by using a double-sided adhesive tape or for example by using a melt adhesive.

The layers of matrix material must be fixed onto the inert support material in such a way that the first layer can be completely separated from the second layer after applying and drying the liquid sample material. This is then possible especially when the first layer is attached only relatively loosely or only at certain points.

The two layers of matrix material must be arranged next to and touching one another on the support material in such a way that a liquid transfer from the first layer into the second layer is possible when the first layer is filled with liquid. This is then possible when there is at least one edge contact of the two layers. However, it is better to provide a slight overlap of the two layers. It is particularly preferable when the layers are arranged such that the second layer slightly overlaps the first layer.

The size of the matrix material layers must be selected such that the first layer which is later also used as the analytical layer can be completely filled with the sample liquid. Excess sample liquid is then taken up by the second layer. Which amounts of sample are adequate for the determination of a particular analyte depends on the type of analyte to be determined. However, 5–20 µl and usually 10 µl sample are adequate as a rule. This volume must be taken up by the first matrix layer and it must be possible to elute it again later. For safety the second matrix layer which has the function of a suction layer must be able to take up a larger volume. Absorption volumes of 10–50 µl, preferably 10–30 µl, particularly preferably 20 µl are usually adequate for this. It is expedient that the usual dimensions of the matrix material layers are such that the absorption volume of the two matrix material layers when taken together is at least 30 µl and preferably at least 50 µl. Such dimensions ensure that the same amount of sample is applied onto the first matrix layer of various elements according to the invention with small as well as with large drops of liquid. The smaller first layer usually has an area of 3×3 to 8×8 mm to achieve an sufficient absorption volume.

The arrangement of the matrix material layers described above enables a homogeneous distribution of liquid sample material in the first layer. Due to the fact that the first layer should be completely filled with liquid sample material, it is not possible for concentration gradients of the analyte to form within this layer which otherwise were always observed in the peripheral zones of the elements of the state of the art. In this way concentration-dependent differences in measurement when determining analytes are avoided.

In order to ensure a separation of the first from the second layer of absorptive matrix material in the element according to the invention, various arrangements of the layers on the support material are conceivable.

Referring to FIG. 1, an element according to the invention carries absorptive matrix material layers (1, 2) at the end of an inert support material (3). The layers are attached to the support material (3) by means of a double-sided adhesive tape (4). The layers (1, 2) are arranged on the support material (3) in such a way that they are located at the end of this support material (3). The first absorptive matrix material layer (1) which is intended for sample application is closest to the end of the support material (3). It is slightly overlapped by the second absorptive matrix material layer (2) which takes up excess liquid from the sample material when the first layer (1) if filled. At the end of the support material (3) below the first layer (1) a recess (5) is located in the support material (3). This recess (5) enables or facilitates the gripping of the first layer (1) for example with tweezers in order to remove this from the element.

In the method according to the invention for analyzing liquid sample material the liquid sample is applied to the first layer of absorptive matrix material (1). Preferably sufficient liquid sample material is applied so that the first layer (1) is completely saturated. It is particularly preferable that as much liquid sample material is applied so that the absorption volume of the first layer (1) is not adequate to completely take up the liquid. The excess liquid reaches the second layer of absorptive matrix material (2) via the first layer (1). The liquid sample material to be examined dries on the element according to the invention and is given to an analytical station in this form. The sample application can be carried out by the patient himself or also by the attending doctor. The analysis is usually carried out in a laboratory. In order to analyse the sample material located on the element, the first layer of absorptive matrix material (1) is removed from the element. In the case of the element according to the invention according to FIG. 1 this can for example be achieved by means of tweezers which grip the first layer (1) in the area of the recess (5) and remove it from the element. In this connection it is apparent that in order to completely remove the first layer (1) of the element this must only be attached so firmly to the support material (3) that it is also possible to completely remove it. In the present case this is ensured by fixing layer (1) only via a narrow strip of double-sided adhesive tape (4) to the inert support material (3) whereas the second matrix material layer (2) is attached via a much larger area with double-sided adhesive tape (4). The complete removability of the first layer (1) ensures that always sample amounts of the same size reach the examination. The layer (1) separated from the element is eluted in order to dissolve the analyte to be determined. For this purpose eluting agents known to a person skilled in the art are used depending on the analyte. The analysis of the resulting solutions is carried out depending on the analyte to be determined and also by methods known by a person skilled in the art. p In another preferred embodiment of the invention according to FIG. 2, the two layers of absorptive matrix material (1, 2) are attached to the inert support material (3) in such a way that two opposite ends of the support material (3) are free and can be gripped by fingers. The two matrix material layers (1, 2) are attached to the support material (3) by double-sided adhesive tape (4, 6). The support material (3) has a pre-determined breaking point (7) which is arranged such that the element can be divided there into two parts by bending, breaking or tearing in such a way that one carries the first layer of absorptive matrix material (1) and the other carries the second layer of absorptive matrix material (2). In the case of a plastic foil as support material (3) the pre-determined breaking point (7) can be an indentation. An appropriate perforation may also, however, be present there which enables two separate parts to be obtained by bending the element at this point.

As much liquid sample material is applied to the first matrix material layer (1) that this layer (1) is completely filled with liquid. The overlapping of the first layer (1) with the second layer (2) ensures that excess liquid reaches the second layer (2). At the analytical station at which the analysis of the sample material is to be carried out, the element is divided at the pre-determined breaking point by bending, breaking or tearing. The part of the element which contains the first layer of absorptive matrix material (1) is treated with eluting agent so that the analyte to be determined is dissolved from the matrix material. The solution obtained in this manner is then analyzed. In this manner contact with the matrix material containing the sample material is completely avoided and the risk of infection is minimized.

Figure 2:
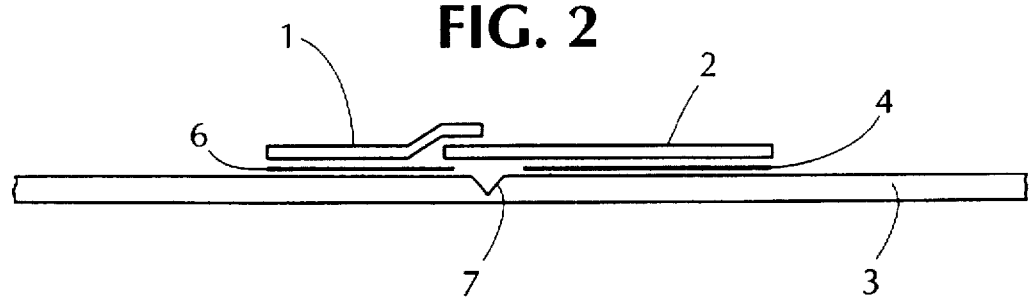
FIG. 2 is a front elevation view of another preferred embodiment of the invention; and, FIG. 3 is a rear view of a system of the invention.

Whereas the element according to the invention according to FIG. 1 has particular advantages for examining blood as well as urine samples, the element according to the invention according to FIG. 2 is very well suited for blood examinations. For examinations of blood the finger of the patient is pricked with a lancet and the drop of blood that emerges is applied to the upper side of the first layer of absorptive matrix material (1) of the element according to the invention. In the case of urine as a sample the side of the element according to the invention according to FIG. 1 which contains the first layer of absorptive matrix material (1) is immersed into the urine in such a way that the second layer of absorptive matrix material (2) is not immersed in the urine.

If necessary, the absorptive matrix material layers of the element according to the invention can carry substances for example to increase the wettability or to stabilize the analyte to be determined. In particular substances for stabilizing the analyte to be determined can be contained in the first layer of the element on which the sample is applied.

Figure 3:
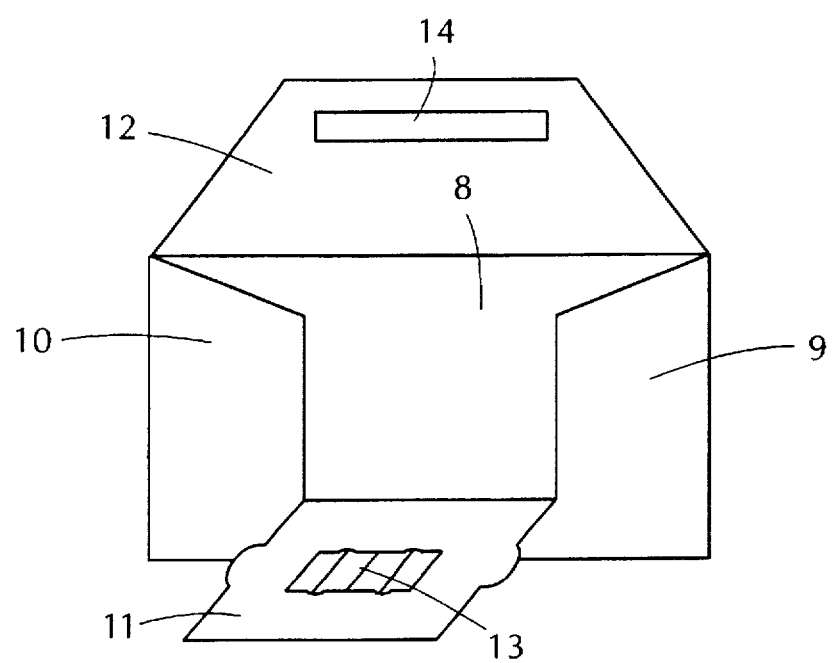

In order to transport the element according to the invention to the analytical station after application of the sample material, it has proven to be expedient to dispatch it within a closable envelope. A specially designed envelope as shown in FIG. 3 is for example suitable as the closable envelope. This envelope contains a front part (8) and two side parts (9, 10) as well as a back flap (11) and a closing flap (12). The element according to the invention for taking up the liquid sample material (13) is secured onto the back flap (11) in a detachable manner so that when the back flap (11) is folded down this element is accessible for the application of the liquid sample material. After application and drying the sample material the back flap (11) is folded up towards the side parts (9, 10) and the front part (8). An adhesive strip (14) is located on the closing flap (12) with which the envelope can be closed after folding down the closing flap (12) over the side parts (9, 10) and the folded up back flap (11). Such an envelope can for example be composed of paper or cardboard. The closable envelope enables a hygienic and clean transport of the element (13) according to the invention containing the sample material to the site at which the sample material is analyzed. At this site the envelope is opened, the back flap (11) is folded down and the element (13) containing the sample material is withdrawn. Subsequently the first and the second layer of absorptive matrix material of the element according to the invention containing the sample material are separated, the first layer is eluted and the dissolved analyte is determined.

The element (13) according to the invention can be detachably fixed to the inside of the back flap (11) in different and numerous ways. For example the element can be clamped by appropriate clamping devices or attached to a double-sided adhesive tape in such a way that it can be detached from the back flap (11) of the envelope in order to analyse the sample material. The element according to the invention and the closable envelope form a system.

The element and system according to the invention are suitable for collecting, storing and transporting sample material to be analyzed. Analytes which can be collected, transported and stored in this manner include glucose and glycosylated haemoglobin ($HbA_{1c}$). However, essentially any analyte can be brought to a measurement which can be removed from the matrix by dissolution by appropriate eluting agents and can then be measured in this solution. In principle these are for example all analytes which can also be determined by immunological test procedures. Without limiting the selection of possible analytes, such analytes include those used to detect infectious diseases such as for example virus antibodies or virus components for the determination of hepatitis and HIV. Samples containing such analytes can be advantageously transported to the site of analysis in this manner. Due to the clean envelope and the hygienic removability of the layer containing the sample material from the element according to the invention, the risk of infection is kept to a minimum. Due to the fact that the absorptive matrix material layer (1) always takes up the same sample volume and that care is taken that this layer is completely filled with liquid sample material and that it, in addition, can be completely reproducibly separated from the second layer of absorptive matrix material, it is ensured that reproducible results of high accuracy are obtained in the subsequent analyses.

The subject matter of the invention is elucidated in yet more detail by the following examples.

EXAMPLE 1

Element according to the invention for absorbing blood which is to be examined for glucose On a polyester foil with the dimensions 48×6 mm having a semi-circle of 5 mm punched out at one of the short-sided ends, a first layer of absorptive matrix material, as shown in FIG. 1, is fixed to the support foil with the aid of a double-sided adhesive tape in such a way that it is fixed to the adhesive tape at a width of 0.5 to 1 mm. The later removal is positively influenced by this relatively narrow attachment. The second layer of absorptive matrix material is glued on at a width of 5 mm or more.

A fleece which has been produced on a paper machine and which has the following technical data is used for the first layer of absorptive matrix material:

100 parts cellulose, degree of grinding 25° SR (degree of drainage capability of a fibre suspension according to notice V/7/61 of the "Verein der Zellstoff und Papier-Chemiker und Ingenieure, Fachausschuβ für physikalische Halbstoff- und Papierprüfung") and 3 parts epichlorohydrin resin as waterproof material, area weight: 100 g/m², absorptive height: 56 mm (DIN 53106).

This fleece is cut to a size of 6×6 mm. This matrix takes up an amount of liquid of 10 µl. This amount has to be known for later calculation of the glucose concentration.

A fleece produced in the same way with the following technical data is used as the second layer of absorptive matrix material:

100 parts cellulose, degree of grinding 31° SR (degree of drainage capability of a fibre suspension according to notice V/7/61 of the "Verein der Zellstoff und Papier-Chemiker und Ingenieure, Fachausschuβ für physikalische Halbstoff- und Papierprüfung") and 3 parts epichlorohydrin resin, area weight: 100 g/m², absorptive height: 42 mm (DIN 53106). This fleece is cut to a size of 18×6 mm.

The patient withdraws an undetermined amount of blood using this element after finger picking by simply holding the first matrix layer to the appearing drop of blood. The amount of blood necessary for later analysis is taken up by the first matrix layer. There is a delayed release of the excess amount of blood to the second layer. The patient inserts the element into a clean envelope and sends it on to the examining laboratory. There the first matrix layer is removed with tweezers and glucose is determined as described for example in Br. Med. J. 2, 468–469 (1978).

EXAMPLE 2

Element for the absorption of blood which is to be examined for haemoglobin and glycosylated haemoglobin ($HbA_{1c}$)

An element of a comparable construction as described in example 1 is produced from the following materials as the absorptive matrix materials:

First layer of absorptive matrix material:
80 parts polyester fibres (fibre diameter 1.7 Dtex), 20 parts viscose, 20 parts polyvinylalcohol, area weight: 80 g/m², absorptive height 102 mm (DIN 53106). This layer takes up an amount of liquid of 15 µl.

Second layer of absorptive matrix material:
80 parts polyester fibres (fibre diameter 3.3 Dtex), 20 parts viscose, 20 parts polyvinylalcohol, area weight: 80 g/m², absorptive height 75 mm (DIN 53106).

The advantage of this fibre mixture is the low polarity due to the fibres. This ensures a good detachment of the haemoglobin and glycosylated haemoglobin which are to be determined.

Deviating from example 1 the two layers are not fixed to the support foil by means of a double-sided adhesive tape but by means of a thin strip of heat-sealing glue. The first layer is fixed over a breadth of 0.5 to 1.0 mm. The second layer can be fixed over a wider area. In the following example 2 mm was selected. Otherwise the procedure is as described in example 1. Haemoglobin and $HbA_{1c}$ are determined for example after elution according to the method described in Klin. Lab. 39, 1080–1082 (1993).

It will be understood that the specification and examples are illustrative but not limitative of the present invention and that other embodiments within the spirit and scope of the inventions will suggest themselves to those skilled in the art.

We claim:

1. An element for collecting, transporting and storing a sample material to be analyzed, the element comprising:

an inert support material; a first and second layer of absorptive matrix material arranged side by side next to and touching one another on the inert support material in a contact enabling transfer of liquid from the first layer into the second layer when the first layer is filled with liquid, the first layer being completely separable from the second layer after having applied the sample material.

2. The element of claim 1 wherein the support material has an end with a recess and the layers of absorptive matrix material are arranged at the end of the support material in such a manner that the first layer is located at the end of the support material so that the first layer can be gripped and removed from the element.

3. The element of claim 1 wherein the support material contains a predetermined breaking location.

4. The element of claim 3 wherein the first and second layers of absorptive matrix material are fixed on the inert support material in such a way that two opposite ends of the support material are free and can be gripped.

5. The element of claim 3 wherein the element can be broken at the predetermined breaking location by bending the element in such a manner that two parts are obtained of which the first carries the first and the other the second matrix material layer.

6. The element of claim 1 wherein the absorptivity of the first layer of matrix material is the same as, or greater than, that of the second layer of matrix material.

7. The element of claim 6 wherein the first layer of matrix material comprises cellulose fibers.

8. The element of claim 1 wherein the first layer comprises polyester fibers, viscose and polyvinylalcohol.

9. A system comprising: an element of claim 1 and a closable envelope in which the element can be transported.

10. The system of claim 9 wherein the envelope has a front part, two side parts, a back flap and a closure flap, said element being securely but detachably, fixed to the back flap of the envelope.

11. The system of claim 10 further comprising means for securing the sample to the back flap of the envelope.

12. The system of claim 11 wherein the means for securing comprise a clamping device or an adhesive tape.

* * * * *

UNITED STATES PATENT AND TRADEMARK OFFICE
CERTIFICATE OF CORRECTION

PATENT NO. : 5,783,759
DATED : July 21, 1998
INVENTOR(S) : Hans Wielinger, et al.

It is certified that error appears in the above-identified patent and that said Letters Patent is hereby corrected as shown below:

In column 2, line 33, move lines 34 through 41 to line 23 after "eluted" and before "Brief Description of the Drawing".

In column 2, line 54, delete "filled".

In column 5, line 14, remove " p ".

Signed and Sealed this

Fourth Day of July, 2000

Attest:

Q. TODD DICKINSON

*Attesting Officer*  *Director of Patents and Trademarks*